United States Patent [19]
White et al.

[11] 3,983,145
[45] Sept. 28, 1976

[54] USE OF ALPHA-DI(LOWER ALKOXY) ANTHRAQUINONES IN THE SYNTHESIS OF ALIZARIN SAPHIROLS

[75] Inventors: David L. White; Joseph W. Fitzpatrick, both of Toms River, N.J.

[73] Assignee: Toms River Chemical Corporation, Toms River, N.J.

[22] Filed: Nov. 1, 1973

[21] Appl. No.: 411,625

[52] U.S. Cl. .................................. 260/373; 8/25; 8/39 C; 252/182; 260/365; 260/368; 260/369; 260/370; 260/371; 260/375; 260/351; 260/512 R; 260/383
[51] Int. Cl.$^2$ .................................. C07C 143/665
[58] Field of Search .......... 260/375, 373, 370, 371, 260/383, 365, 368, 369, 512 R, 351; 8/25, 39 C; 252/182

[56] References Cited
UNITED STATES PATENTS
1,859,583  5/1932  Crowell ............................. 260/375
1,924,166  8/1933  Rogers ............................. 260/375

OTHER PUBLICATIONS
Barnett, Anthracene and Anthraquinone, D. Van Nostrand Co. N.Y., N.Y., 1921, p. 288.
Kirk–Othmer (I) Encyclopedia of Chemical Technology, Interscience, vol. 2, p. 469, 491, 492.
Kirk–Othmer (II) Encyclopedia of Chemical Technology, vol. 8, p. 473.
Huffmann, Defensive Publication 8670g1094.
Beilstein, vol. 8, p. 454, 459.
Lubs. The Chemistry of Synthetic Dyes and Pigments, A.C.S. Monograph 1955, p. 350–355, 359.

Primary Examiner—Arthur P. Demers
Attorney, Agent, or Firm—Joseph G. Kolodny; Edward McC. Roberts; Prabodh I. Almaula

[57] ABSTRACT

Alpha-dihydroxyanthraquinones used as intermediates in the synthesis of many dyestuffs, such as the Alizarin Saphirols (e.g. Color Constitution No. 63000, 63005, 63010, 63011, 63315 and 63610) can be replaced on an equimolar basis by alpha-di(lower alkoxy)anthraquinones. The alpha-di(lower alkoxy) anthraquinones can be converted in a single step, by treatment with oleum, to the corresponding alpha-dihydroxyanthraquinone-beta-disulfonic acids in almost quantitative yield. The corresponding diamine is obtained by dinitrating followed by reduction of the nitro groups. The known intermediate, leuco 1,4,5,8-tetrahydroxyanthraquinone (see C.I. No. 62500) can be obtained either by reduction of the diamine or by reduction of the dinitro compound. In one embodiment, the alpha-di(lower alkoxy)anthraquinone is obtained from dinitroanthraquinone by treatment thereof with methanol and KOH.

6 Claims, No Drawings

USE OF ALPHA-DI(LOWER ALKOXY) ANTHRAQUINONES IN THE SYNTHESIS OF ALIZARIN SAPHIROLS

BACKGROUND OF THE INVENTION 1,5- and 1,8-dihydroxyanthraquinone, as well as mixtures thereof, are important intermediates in the manufacture of a large number of dyestuffs. One synthetic route to those compounds involves the conversion of the anthraquinone disulfonic acid to the dihydroxyanthraquinone by treatment of the disulfonic acid with $Ca(OH)_2$ and $MgCl_2$ at a temperature of 215°–230°C (c.f. Lubs, The Chemistry of Synthetic Dyes and Pigments, 1955 Reinhold Publishing Corp., pages 367–368). The mixed 1,5- and 1,8-anthraquinone disulfonic acids can be obtained by sulfonating anthraquinone with 36–40% oleum in the presence of mercury catalyst. The 1,5 isomer can be salted out from the more soluble 1,8 isomer after dilution. In connection with this synthesis, however, the use of mercury catalyst presents the problem of disposing of a mercury-contaminated reaction medium, which disposal is attended by rather serious ecological considerations.

Direct dinitration of anthraquinone, separation of the 1,5- isomer and conversion of the nitro group to the hydroxyl group has not been acceptable since there are produced about 20% of isomeric nitro compounds that are difficult to separate and remove.

It is apparent that one desirous of preparing alphadihydroxyanthraquinones is confronted by the proposition that, in order to obtain a high quality product, it is necessary to use a route that results in an unacceptable environmental impact while, on the other hand, the attempt at a different route results in a mixture of isomers whose resolution is difficult and expensive.

DESCRIPTION OF THE INVENTION

It has now been found that, in connection with the synthesis of many anthraquinone compounds, the independent preparation of the alpha-dihydroxyanthraquinones can be eliminated, that the hitherto unacceptable direct nitration of anthraquinone can be employed successfully and that the dyestuffs obtained display substantially the same yield, purity and dyeing characteristics as dyestuffs prepared by the processes conventional in the art. It has additionally been found that alpha-di(lower alkoxy)anthraquinones will undergo cleavage and sulfonation to provide the corresponding alpha-dihydroxyanthraquinone-beta-disulfonic acids.

In one aspect, this invention relates to a process for making alpha-dihydroxyanthraquinone-beta-disulfonic acids which comprises treating an alpha-di(lower alkoxy)anthraquinone with oleum at from 80° to 155°C.

In another aspect, the invention relates to a composition which comprises from 40 to 60% by weight of 1,5-dimethoxyanthraquinone and correspondingly from 30 to 50% by weight of 1,8-dimethoxyanthraquinone. In yet another aspect, the invention relates to a composition which comprises from 40 to 60% by weight of 1,5-dihydroxyanthraquinone-2,6-disulfonic acid and correspondingly from 30 to 50% by weight of 1,8-dihydroxyanthraquinone-2,7-disulfonic acid.

In one embodiment, the invention relates to a process for making 1,5-dihydroxy-4,8-diaminoanthraquinone-2,6-disulfonic acid, which comprises treating a mixture of 1,5-di(lower alkoxy) anthraquinone and 1,8-di(lower alkoxy)anthraquinone with oleum, thereafter dinitrating the resulting anthraquinone, separating 1,5-dihydroxy-4,8-dinitroanthraquinone-2,6-disulfonic acid from the reaction medium and thereafter reducing the nitro groups to amine groups to yield 1,5-dihydroxy-4,8-diaminoanthraquinone-2,6-disulfonic acid. In another embodiment, the invention relates to a process for making mixed 1,5-dihydroxy-4,8-diaminoanthraquinone-2,6-disulfonic acid and 1,8-dihydroxy-4,5-diaminoanthraquinone-2,7-disulfonic acid which comprises treating a mixture of 1,5-di(lower alkoxy)anthraquinone and 1,8-di(lower alkoxy)anthraquinone with oleum, thereafter dinitrating the resultant anthraquinones and then reducing the nitro groups to amine groups to yield the indicated mixture. In still another embodiment, the invention involves a process for making leuco-1,4,5,8-tetrahydroxyanthraquinone, which comprises treating a mixture of 1,5-di(lower alkoxy)anthraquinone and 1,8-di(lower alkoxy)anthraquinone with oleum, dinitrating the resulting anthraquinones and thereafter reducing the nitro groups to amine groups, followed by reduction to obtain the leuco-tetrahydroxyanthraquinone. The leuco-tetrahydroxyanthraquinone can also be obtained from the dinitroanthraquinone by reduction without intermediate recovery of the amine, and can be obtained from the 1,5-dihydroxy-4,8-dinitroanthraquinone-2,6-disulfonic acid, the 1,8-dihydroxy-4,5-dinitroanthraquinone-2,7-disulfonic acid or mixture thereof. In still another aspect, the invention relates to an improvement in a process for making 1,5-dihydroxy-4,8-diaminoanthraquinone-2,6-disulfonic or 1,8-dihydroxy-4,5-diaminoanthraquinone-2,7-disulfonic acid or mixture thereof which comprises nitrating anthraquinone to introduce two nitro groups per molecule, thereafter treating a product of said nitration step with methanolic caustic to replace the nitro groups by methoxy groups and thereafter treating the methoxylated product with oleum to form the dihydroxyanthraquinonedisulfonic acid.

An important aspect of this invention is the discovery that alpha-loweralkoxyanthraquinones, and especially alpha-di(lower alkoxy)anthraquinones can be cleaved and sulfonated by treatment with oleum to provide the corresponding alpha-hydroxyanthraquinone-beta-sulfonic acid. In the case of the alpha-di-(lower alkoxy)anthraquinones, the cleavage and sulfonation reactions take place at virtual quantitative levels; the reaction is characterized by the substantial absence of side reactions, formation of undesirable isomers and the like. This in itself is considered to be wholly surprising and altogether unpredictable.

The alpha-(lower alkoxy)anthraquinones and especially the alpha-di(lower alkoxy)anthraquinones can come from any convenient source. One convenient method for preparing the lower alkylanthraquinone ethers useful herein is a well-known variation of the Williamson synthesis, wherein a dialkyl sulfate is used to alkylate an aromatic hydroxyl group in the presence of alkali at moderate temperatures. Another convenient mode of synthesis of the alpha-lower alkoxyanthraquinones is by displacement of various substituents in substituted anthraquinones. Typically, one can replace —Cl, —$SO_3H$ and —$NO_2$ groups with an ether by reaction with a lower alkanol, such as methanol, in caustic, such as potassium hydroxide. The art demonstrates a clear preference for replacing —Cl and —$SO_3H$ because the reactions introducing these groups are far more specific than is the reaction introducing the nitro group. As regards the step of cleavage and sulfonation described herein, however, the source of the anthraquinone ether is not deemed significant. It is preferred, however, that the ether be an alpha-lower alkoxyanthraquinone and especially an alpha-di(lower alkoxy)anthraquinone. Further, it is particularly preferred that the alkoxy substituents contain from 1 to 4 carbon atoms. Especially preferred are methoxy and ethoxy.

The following illustrate some of the known variations of the Williamson synthesis whereby the alpha-lower alkoxyanthraquinones can be prepared:

a. Reaction of a dialkyl sulfate with an alkali metal salt of an alpha-dihydroxyanthraquinone

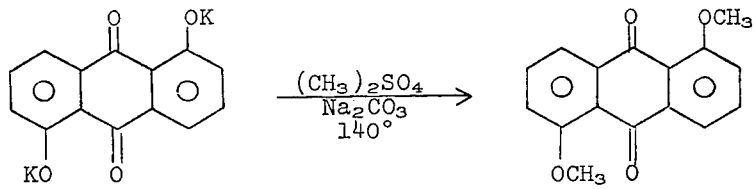

Reference: J. Chem. Soc. 1931, pp. 164–66

Although the 1,5-isomer is shown, the reaction is applicable to the 1,8-isomer, as well as mixtures of said isomers. Other lower alkyl ethers can be obtained by using an appropriate sulfate, such as diethyl sulfate, dipropyl sulfate, etc.

b. Reaction of an alkyl halide with an alkali metal salt of an alpha-dihydroxyanthraquinone

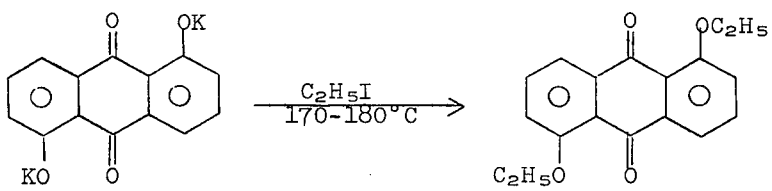

Reference: Ber. 35, 2939

Again, use of other lower alkyliodides will yield other lower alkyl ethers. Although the 1,5-isomer is shown, the 1,8-isomer or mixture of said isomers can be used.

c. Reaction of alkali metal alkoxides with a halogenated anthraquinone

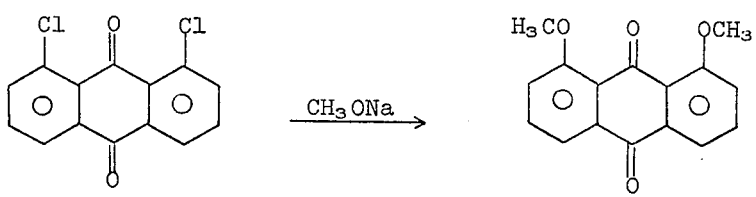

Reference: Frdl. 10, pp. 592–3

The 1,5-isomer can be used, as can mixtures of alpha-isomers; other lower alkyl ethers can be obtained by use of the appropriate lower alkoxide.

Alpha-sulfoanthraquinones can be converted to the corresponding ether by reaction with a lower alkanol in caustic:

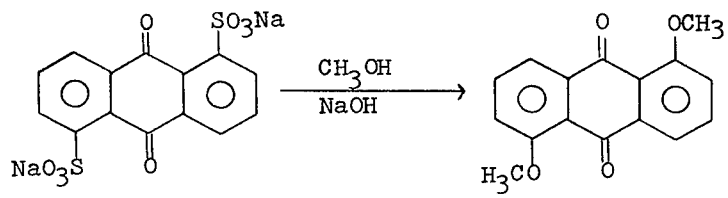

Reference: Ber. 63, 3048
Frdl. 8, 240

As indicated above, it has been found that alpha-lower alkoxyanthraquinones, especially alpha-di(lower alkoxy) anthraquinones, can be cleaved and sulfonated to provide the corresponding alpha-hydroxyanthraquinone-beta-sulfonic acid. More particularly, it has been found that alpha-di(lower alkoxy) anthraquinones and especially 1,5-di(lower alkoxy)anthraquinone, 1,8-di(-lower alkoxy)anthraquinone and mixtures thereof can be cleaved and sulfonated in a single step to afford the corresponding alpha-dihydroxyanthraquinone-beta-disulfonic acid in almost quantitative yield with substantially no formation of other isomeric sulfonic acids.

The sulfonation-cleavage reaction is achieved by contacting an alpha-loweralkoxyanthraquinone with oleum at a temperature of from about 80° to 155°C, preferably from about 130° to about 140°C, for a period of from 2 to 6 hours, preferably for about 3 to 4 hours.

The oleum, of course, is a mixture of $SO_3$ in $H_2SO_4$ and it can contain from about 1% to about 25% $SO_3$, preferably from about 10% to about 12% $SO_3$. The mole ratio of $H_2SO_4$ to alpha-loweralkoxyanthraquinone, while not critical so long as there is an excess of $SO_3$, is desirably about 5 to 6 moles of $H_2SO_4$ per mole of anthraquinone. As indicated, the reaction, especially in the case of the alpha-di(lower alkoxy) anthraquinones proceeds smoothly, substantially without formation of isomeric sulfonation products. The resulting alpha-hydroxyanthraquinone-beta-sulfonic acid can be worked up and recovered in any convenient manner.

As indicated, a preferred embodiment of the invention involves the application of the sulfonation-cleavage reaction described to a process for making the Alizarin Saphirols from anthraquinone. Contrary to the conventional wisdom of the art, it is now possible to use dinitroanthraquinone as a starting material in the synthesis of these Alizarin Saphirols, as well as the synthesis of leuco-tetrahydroxyanthraquinone.

The following will carry a synthesis, beginning with nitration of anthraquinone through to the preparation of useful products and will describe this aspect of the invention in greater detail.

The initial step in the synthesis described herein is the dinitration of anthraquinone, according to the following equation:

The dinitration of anthraquinone is a reaction that is well-known in the art. Reference is had to the Kirk-Othmer Encyclopedia of Chemical Technology, Second Edition, 1963, John Wiley and Sons, Inc., page 490, as well as to the article by Hefti, Helv. Chim. Acta 14, 1404–1405 (1931) mentioned therein. It is indicated that in the dinitration of anthraquinone, there is obtained 41% of the 1,5- isomer; 38% of the 1,8-isomer and about 15% of mixed 1,6- and 1,7-dinitroanthraquinone. Kirk-Othmer, at pages 491 and 492, provide a synthesis of 1,5- and 1,8-dinitroanthraquinone. Reference is also had to Lubs, The Chemistry of Synthetic Dyes and Pigments, Reinhold Publishing Corp., 1955, page 350.

The next step in the process involves the conversion of nitro groups to lower alkoxy groups by treating the dinitro compounds with lower alkanolic caustic. Representative lower alkanols include methanol, ethanol, isopropanol, t-butanol, etc. Methanol is preferred. The caustic is preferably an alkali metal hydroxide; KOH is preferred. The reaction can be conducted at a temperature of from 65° to 120°C, preferably from 80° to 100°C. The concentration of caustic is about 11.5% by weight, to provide a mole ratio of 2–3 moles of caustic per mole of dinitroanthraquinone. The product of the reaction comprises 40–60% 1,5-dimethoxyanthraqui-

I.

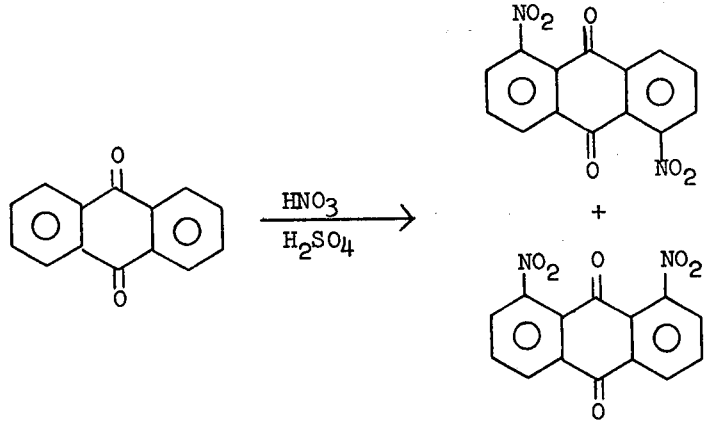

none and correspondingly about 30–40% 1,8-dimethoxyanthraquinone. The reaction is as follows:

II.

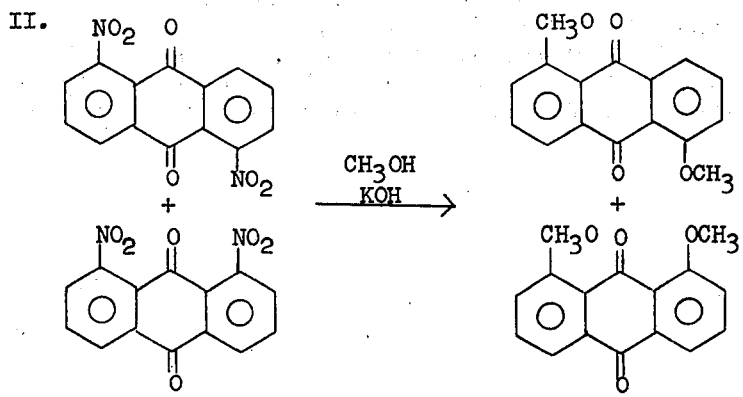

The mixture of dimethoxyanthraquinones can be saponified and sulfonated in a single step to form the dihydroxyanthraquinonedisulfonic acid, according to the following equation:

of 1,5-dihydroxy-4,8-dinitroanthraquinone-2,6-disulfonic acid, from 20 to 40% of 1,8-dihydroxy-4,5-diaminoanthraquinone-2,7-disulfonic acid and up to 20% of other isomers.

III.

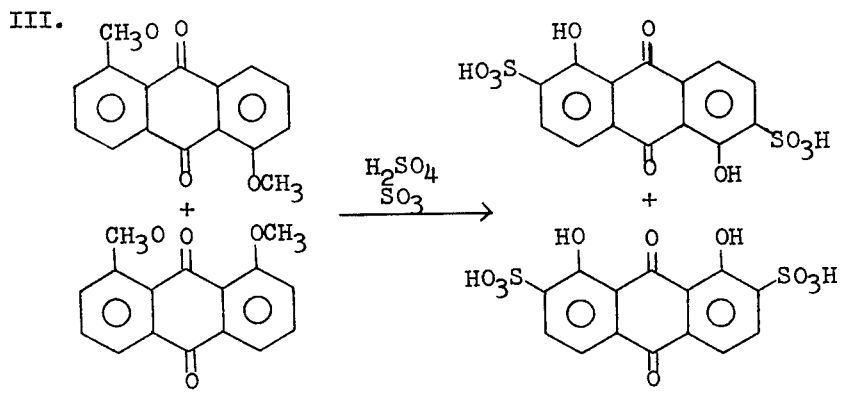

The conditions for the cleavage-sulfonation reaction are as previously described.

If desired, the 1,5-dihydroxyanthraquinone-2,6-disulfonic acid can be separated from the 1,8-dihydroxyanthraquinone-2,7-disulfonic acid. However, the fractional salting out is not desirable at this stage.

The mixture of dihydroxydisulfonic acids, after separation, is nitrated in known manner according to the following equation:

Although it is possible to nitrate in situ immediately following the sulfonation step, this is not a preferred or even desirable mode of preceeding. In the removal of the methoxy groups, dimethylsulfate and/or methylsulfuric acid probably forms. If the reaction medium were nitrated, the explosive compound, methyl nitrate, may form. It is, therefore, preferred to conduct the sulfonation-cleavage reaction as a step separately from the nitration step.

IV.

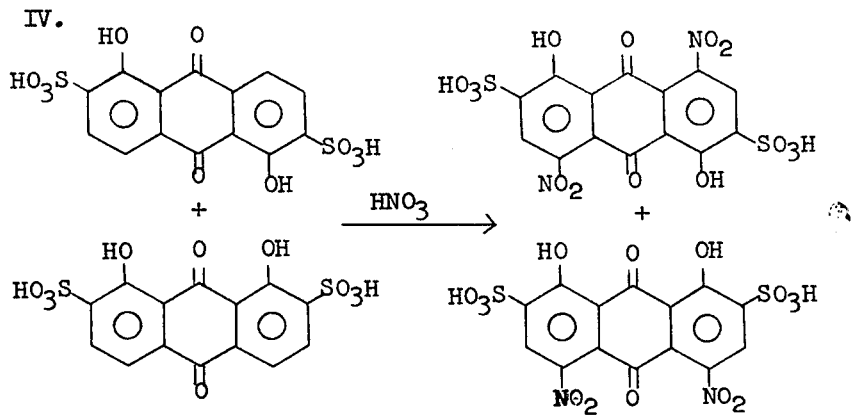

The nitration can be conducted in the presence of sulfuric acid at a temperature of from about 20° to about 60°C, preferably of from about 40° to 45°C over a period of 1 to 4 hours, preferably about 2 hours. The mole ratio of anthraquinone:$HNO_3$:$H_2SO_4$ can be from 1:2:10 to 1:4:15. A convenient ratio is 1:2.5:14. These ratios are not critical. The product will contain 40–60%

At this stage, the 1,5-dihydroxy-4,8-dinitroanthraquinone-2,6-disulfonic acid can be readily separated by salting out from the 1,8-dihydroxy-4,6-dinitroanthraquinone-2,7-disulfonic acid, if desired.

The 1,5-dihydroxy-4,8-dinitroanthraquinone-2,6-disulfonic acid can be reduced in known manner to yield the corresponding diamine according to the following equation:

V.

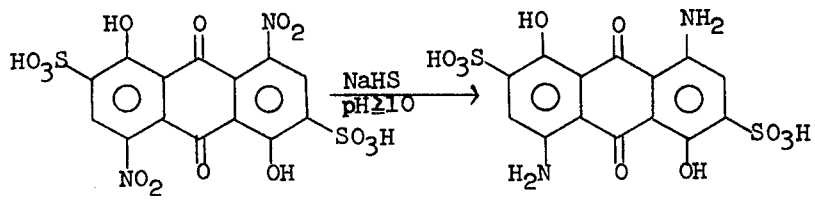

The pH of the system can be maintained strongly basic (pH=10+) with any convenient alkali, such as with the alkali and alkaline earth metal hydroxides and carbonates. The mole ratio of anthraquinone:caustic:-NaHS can range from 1:5–6:3–6, with sufficient water present to afford good stirring. Contact is maintained at 80°–100°C, preferably at 100°C for 15 minutes to 1 hour.

Alternatively to separating the dinitro isomers, the mixture can be reduced to yield the mixed diamino anthraquinones according to the following equation:

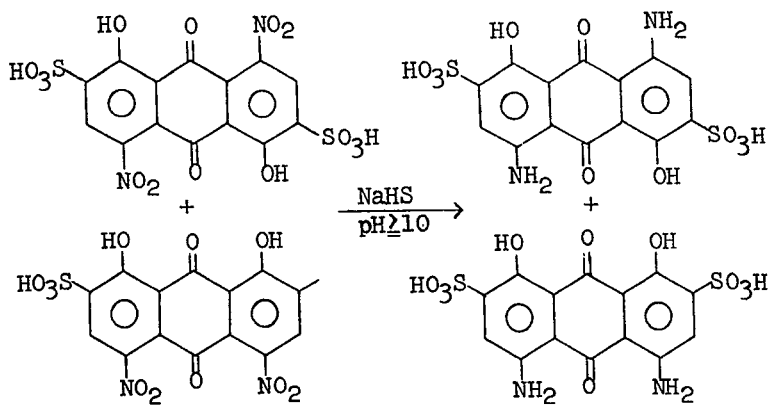

The reaction conditions are as described above.

The mixture of 1,5-dihydroxy-4,8-diaminoanthraquinone-2,6-disulfonic acid and 1,8-dihydroxy-4,6-diaminoanthraquinone-2,7-disulfonic acid can be further reduced to yield leuco 1,4,5,8-tetrahydroxyanthraquinone according to the following equation:

be 1:14–16:3–5 and is not deemed critical. The reaction temperature can range from 80° to 100°C and is preferably at 100°C for a period of 30 to 90 minutes, preferably 60 minutes. There is obtained the tetrasodium salt of leuco-tetrahydroxyanthraquinone in about 70% yield.

When the alpha-dimethoxyanthraquinones derived from the dinitration products of anthraquinone are substituted on an equimolar basis for a commercially available mixture of 1,5-dihydroxyanthraquinone and 1,8-dihydroxyanthraquinone containing no appreciable amounts of other isomeric anthraquinones and worked up to provide the mixed diamino anthraquinones of equation VI (Alizarine Saphirols), it is found that there is obtained substantially the same quantitative yield of dyestuff that provides comparable dyeing strengths and shades at the same dyestuff levels. In view of the fact that direct nitration of anthraquinone yields some 15 to 20% of undesirable isomers, these discoveries are altogether surprising and unexpected.

The invention described herein will be further illuminated by the following examples.

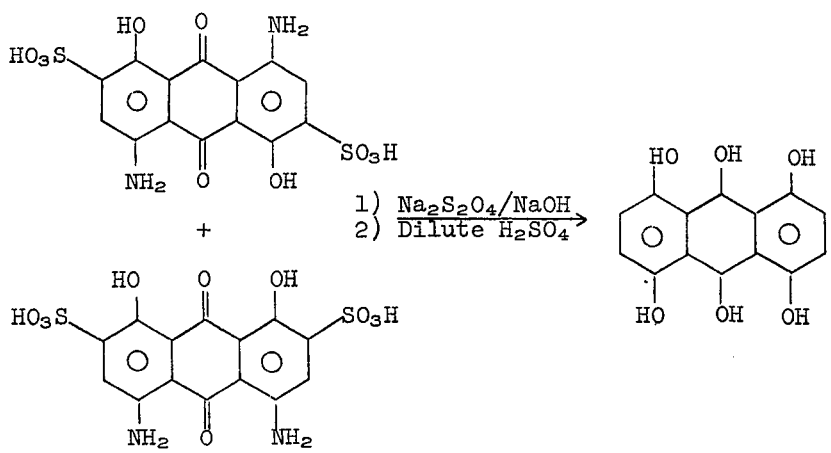

The reaction of the diamine to the leuco-tetrahydroxyanthraquinone is accomplished in known manner by $Na_2S_2O_4$ under strongly alkaline conditions obtained by use of an alkali metal hydroxide.

The ratio of anthraquinone:hydroxide:$Na_2S_2O_4$ can

EXAMPLE 1

This example illustrates the dinitration of anthraquinone.

650 Parts of anthraquinone were dissolved in a mixture of 2,950 parts by weight of 96% sulfuric acid and 2,050 parts by weight of 25% oleum (75% $H_2SO_4$ - 25% $SO_3$ by weight). To this solution was added drop-wise at 28°-33°C 1,100 parts of mixed acid (50:50 $H_2SO_4$:$HNO_3$ by weight). The resulting mixture was stirred at 30°-33°C for 2 hours, heated to 91°C over 1½ hours and then stirred at 91° to 93°C for an additional three hours.

The reaction mixture was filtered and washed with three 250 parts portions of 90% sulfuric acid. The resulting cake was slurried in water, filtered and washed with water until neutral. Upon drying, there were obtained 682 parts of dinitroanthraquinone, containing 50–60% of 1,5-dinitroanthraquinone, 30–40% of 1,8-dinitroanthraquinone and up to 20% of other isomers.

EXAMPLE 2

This example illustrates the conversion of dinitroanthraquinone to dimethoxyanthraquinone.

630 Parts of dinitroanthraquinone prepared as in Example 1 above were slurried in a solution of 292 parts of potassium hydroxide in 2,000 parts of methanol. This slurry was charged to a 4-liter stirred autoclave which was thereafter purged with an inert gas and sealed. The autoclave was heated to 80°C over 2 hours, held at 80°C for an additional 2 hours, heated to 100°C (about 40 psi pressure) and held at 100°C for an additional five hours. The reaction mixture was then drowned into 5,500 parts of water and this drowned mixture was refluxed for one hour before being filtered. The brown, crystalline product was washed neutral with water and dried to yield 479 parts of dimethoxyanthraquinone which represents a yield of 85% of theoretical. The product contains 50–60% of 1,5-dimethoxyanthraquinone, 30–40% of 1,8-dimethoxyanthraquinone and up to 20% of other isomers.

EXAMPLE 3

This example illustrates the cleavage and sulfonation of the dimethoxyanthraquinones.

To a mixture of 168 parts of 96% sulfuric acid and 50 parts of 25% oleum were added incrementally 97 parts of dimethoxyanthraquinone prepared as in Example 2. The resulting suspension was treated drop-wise at a temperature below 40°C with 270 parts of 25% oleum. The reaction mixture was then heated to 138 to 140°C over 2 hours and held at that temperature for an additional four hours. At the end of the heating period, the reaction mixture was cooled to below 100°C and drowned into 1,500 to 2,000 parts of water. The resulting mixture was clarified with the aid of diatomaceous earth and charcoal; clarification at this point is optional and can be dispensed with, if desired.

a. Recovery of the Mixed Salt

The clarified solution obtained as above was added to a mixture of 150 to 250 parts of potassium sulfate and 1,500 to 2,000 parts of hot water. The resulting mixture was cooled to 0° to 30°C. Ater stirring for several hours at 0° to 30°C, the mixture was filtered. The solid obtained was washed neutral with dilute potassium sulfate solution and the neutral cake dried.

b. Resolution of 1,5- and 1,8-dihydroxy isomers

The clarified solution obtained as described above was cooled to 25°C and drowned into 8,000 parts of water. The resulting solution was heated to 95° to 100°C and treated with a solution of 1,570 parts of KCl in 2,780 parts of hot water. A golden yellow crystalline precipitate was immediately formed and was isolated by filtration at 95°C and thereafter washed with saturated KCl solution and dried to give 134 parts of product. Its infrared spectrum and paper chromatogram were identical to those obtained by di-sulfonating 1,5-dihydroxyanthraquinone.

The filtrate from the above filtration was allowed to cool slowly to 25°C. A yellow, crystalline solid precipitated. It was isolated by filtration, washed with saturated KCl solution and dried to give 120 parts of product. Its infrared spectrum and paper chromatogram are identical to the product obtained by di-sulfonating 1,8-dihydroxyanthraquinone.

EXAMPLE 4

This example illustrates the nitration of the dihydroxyanthraquinonedisulfonic acid. As has been indicated previously, it is preferred to separate the sulfonation and nitration steps because of the danger of the formation of explosive methylnitrate.

The dried product obtained as in Example 3a) above was added to 292 parts of 96% sulfuric acid and 208 parts of 25% oleum. To this mixture was added drop-wise at 20° to 30°C 94 parts of mixed acid (50:50 $HNO_3$:$H_2SO_4$ on a weight basis). The reaction mixture was then stirred at about 30°C for 30 minutes, heated to 45°C over about an hour and stirred at 45°C for an additional 2 hours.

a. Recovery of Mixed Isomers

The above nitration mass was drowned into a solution of 150 parts of potassium sulfate in 2,500 parts of water. The resulting mixture was allowed to cool to 0° to 30°C. After stirring for about 4 hours at 0° to 30°C, the mass was filtered and the cake recovered.

b. Resolution of 1,5- and 1,8-dihydroxy Isomers

A nitration mass obtained as above was drowned into a solution of 150 parts of potassium sulfate and 2,500 parts of water. The drowned mixture was heated to 95°C and was then filtered at 90° to 70°C on a heated funnel. The solid deposited on the funnel was dipotassium 1,5-dihydroxy-4,8-dinitroanthraquinone-2,6-disulfonic acid containing less than 1% of the corresponding 1,8-isomer. The infrared spectrum and paper chromatogram were identical to those of dipotassium 1,5-dihydroxy-4,8-dinitroanthraquinone-2,6-disulfonic acid prepared from 1,5-dihydroxyanthraquinone.

The filtrate obtained was cooled to room temperature, was further cooled to 0° to 30°C, and was held at that temperature for about four hours. Filtration of the cold mixture yielded dipotassium 1,8-dihydroxy-4,5-dinitroanthraquinone-2,7-disulfonic acid containing a trace (0–10%) of the 1,5-isomer. The infrared spectrum and paper chromatogram were equivalent to those of 1,8-dihydroxy-4,5-dinitroanthraquinone-2,7-disulfonic acid dipotassium salt prepared from 1,8-dihydroxyanthraquinone.

EXAMPLE 5

This example illustrates the reduction of the nitro compounds to amine compounds.

a. Mixed 1,5/1,8 Product

The filter cake obtained as in Example 4a) was suspended in a solution of 210 parts of sodium carbonate and 2,500 parts of water. This alkaline suspension was treated with 110 parts of sodium sulfhydrate and heated to 100°C. The dark blue suspension thus obtained was held at about 100°C for 30 minutes (with addition of additional sodium sulfhydrate if necessary to provide an excess of sulfide ions in the reduction mixture).

The reaction mixture was cooled to 70°C and filtered. The resulting blue solid was washed sulfide-free with dilute brine. Drying of this cake yielded about 130 parts of a mixture of 1,5/1,8-dihydroxy-4,8/4,5-diaminoanthraquinone-2,6/2,7-disulfonic acid, disodium salt.

b. Preparation of 1,5-dihydroxy-4,8-diaminoanthraquinone-2,6-disulfonic acid salt Dipotassium 1,5-dihydroxy-4,8-dinitroanthraquinone-2,6-disulfonic acid, obtained as in Example 4b) was suspended in a solution of 150 parts of sodium carbonate in 1,800 parts of water. This alkaline suspension was treated with 75 parts of sodium sulfhydrate and heated to 100° to 102°C. After 30 minutes at this temperature, the reaction mixture was cooled to 70°C and filtered. The dark blue product was washed with dilute brine and dried to yield about 80 parts of dry color. Spectrophotometric and paper chromatographic analyses indicated that the product contained approximately 70 parts of 1,5-dihydroxy-4,8-diaminoanthraquinone-2,6-disulfonic acid salt and less than 1% of the 1,8-isomer.

c. Preparation of 1,8-dihydroxy-4,5-diaminoanthraquinone-2,7-disulfonic acid salt Dipotassium 1,8-dihydroxy-4,5-dinitroanthraquinone-2,7-disulfonate obtained in Example 4b was suspended in a solution of 63 parts of sodium carbonate and 750 parts of water. This alkaline suspension was treated with 33 parts of sodium sulfhydrate, heated to 100° to 102°C and held at that temperature for 30 minutes. At the end of this period, the reaction mixture was cooled to 70°C and filtered. The dark blue product was washed with dilute brine and dried to yield about 30 parts of dry color. Paper chromatography indicated that this material is 1,8-dihydroxy-4,5-diaminoanthraquinone-2,7-disulfonic acid salt containing a trace of the 1,5-isomer.

d. Comparative Dyeing Test of Mixed 1,5/1,8 Saphirol 87 grams of a commercially available mixture of 56% 1,5-dihydroxyanthraquinone and 41% 1,8-dihydroxyanthraquinone were worked up in parallel with an equal molar amount of the mixed 1,5/1,8-dimethoxyanthraquinone obtained as in Example 2, to yield the products of Example 5a. The results are summarized in Table 1 below.

TABLE 1

|  | Commercial[1] 1,5/1,8-dihydroxy | Experimental[1] 1,5/1,8-dimethoxy |
|---|---|---|
| Yield of dry color | 133 grams[5] | 127 grams[6] |
| Dyeing strength[2] | ~84 | ~84 |
| Shade, range[3] [4] | Trace to Slightly Red | Trace Red to Trace Green |
|  | Trace to Slightly Bright | Trace Bright |
| Acetate stain, range[3] [4] | Trace Green | Slightly Red to Slightly Green |

[1] Average of 8 runs
[2] Parts by weight to equal 100 parts of standard
[3] Standard=Commercially available Alizarine Blue B (Acid Blue 45)
[4] According to Standard Commercial Practice
[5] Based on 87 grams of a mixture containing 56% 1,5-dihydroxyanthraquinone and 41% 1,8-dihydroxyanthraquinone
[6] Based on 97 grams of a mixture of 1,5/1,8-dimethoxyanthraquinones prepared as in Example 2.

It is seen that there is obtained an equivalent amount of dry color having approximately equal dyeing strength and shade.

The 1,5-dihydroxy-4,8-diaminoanthraquinone-2,6-disulfonic acid prepared as described herein can further be used to make the disperse dyes described in U.S. Pat. Nos. 1,903,862; 3,043,646; 3,265,709; 3,349,104 and British Pat. No. 1,024,036.

e. Preparation of C. I. Acid Blue 43

The mixed 1,5/1,8-dihydroxy-4,8/4,5-diaminoanthraquinone-2,6/2,7-disulfonic acid prepared as in Example 5a was converted into C. I. Acid Blue 43, Colour Constitution No. 63,000 by reduction with hydrosulfite and compared with the comparable compound prepared from a commercially available mixture of 56% 1,5-dihydroxyanthraquinone and 41% 1,8-dihydroxyanthraquinone.

A vessel was charged with 300 parts of water and heated to 60°–70°C. Sufficient Saphirol cake was added to provide an amount comparable to 130.5 parts of commercial Alizarine Blue B Standard. The cake was stirred to form a slurry and an additional 100–200 parts of water were added to form a smooth, lump-free slurry. The mixture was diluted to provide about 2,400 parts and heated to 70°C. Agitation was increased and 10.5 parts of hydrosulfite were quickly added, followed by 21.5 parts of sodium carbonate. Rapid agitation was maintained for 10–15 minutes at 70°C, at the end of which period agitation was slowed and 120 parts of sodium chloride added. The mixture was cooled to 40°C, filtered and then washed with 800 parts of 5% NaCl solution. The results are summarized in Table 2 below.

TABLE 2

| C.I. Acid Blue 43 | Based on Commercial 1,5/1,8-dihydroxy | Based on 1,5/1,8-dimethoxy |
|---|---|---|
| Yield dry color | 66.6 grams | 75.5 grams |
| Dyeing strength[2] [1] | 92 | 98 |
| Shade[3] [1] | Dist. Green Sl Bright | Dist. Green Sl Bright |
| Acetate stain[3] [1] | Superior to Std. | Superior to Std. |

[1] Standard=Commercially available Alizarine Blue SE (C.I. Acid Blue 43)
[2] Weight of dye to equal 100 parts standard
[3] According to Standard Commercial Practice

EXAMPLE 6

This example illustrates the formation of leuco 1,4,5,8-tetrahydroxyanthraquinone.

a. The mixed 1,5/1,8-dihydroxy-4,8/4,5-diaminoanthraquinone-2,6/2,7-disulfonic acid disodium salt prepared according to Example 5a was diluted with 1000 parts of water and 390 parts of 50% aqueous sodium hydroxide solution. It was then treated incrementally with 195 parts of sodium hydrosulfite and heated to 98° to 100°C. After 1 hour at that temperature the brown-black reaction mixture was filtered and rinsed with dilute sodium sulfate solution containing about 1% of sodium hydrosulfite. This presscake was immediately acidified by slurrying in a solution of 118 parts of concentrated sulfuric acid and 750 parts of water. Filtration of this slurry yielded a dark brown presscake which contained 66% solids. The paper chromatogram of this product was equivalent to that of commercially available leuco 1,4,5,8-tetrahydroxyanthraquinone.

b. The 1,8-dihydroxy-4,5-diaminoanthraquinone-2,7-disulfonic acid reaction mixture prepared as in Example 5c, was cooled to 70°C. It was then treated with 117 parts of 50% sodium hydroxide solution and 70 parts of sodium hydrosulfite. The mixture was heated to 78° to 100°C and held at that temperature for 1 hour. It was then cooled to 60°C and filtered. The product was washed with dilute sodium sulfate solution containing about 1% of sodium hydrosulfite and the washed cake was immediately slurried in 10 to 15% sulfuric acid. The filtration of the product and drying yielded 20 parts of leuco 1,4,5,8-tetrahydroxyanthraquinone.

c. Mixed 1,5/1,8-dihydroxy-4,8/4,5-dinitroanthraquinone-2,6/2,7-disulfonic acid dipotassium salt can be converted into leuco 1,4,5,8-tetrahydroxyanthraquinone directly, without intermediate recovery of the amine.

A reaction mixture obtained as in Example 5a was cooled to 70°C and treated with 390 parts of 50% aqueous sodium hydroxide solution followed by 195 parts of sodium hydrosulfite. The resulting mixture was heated to 98° to 100°C and held at that temperature for 1 hour. It was then cooled to 60°C and filtered. The product was washed with dilute sodium sulfate solution containing about 1% of sodium hydrosulfite. It was then acidified by slurrying in a 10 to 15% sulfuric acid solution. Filtration, washing and drying yielded 64 parts of leuco 1,4,5,8-tetrahydroxyanthraquinone which yielded a paper chromatogram equivalent to that of the commercially available material.

d. Comparison with Commercial 1,5/1,8-dihydroxyanthraquinone

87 Parts of a substantially pure mixture of 1,5-dihydroxyanthraquinone and 1,8-dihydroxyanthraquinone and 97 parts of mixed 1,5/1,8-dimethoxyanthraquinones obtained as in Example 2 above were worked up in accordance with Example 6c to synthesize the leuco-tetrahydroxyanthraquinone; the results are summarized in Table 3 below.

TABLE 3

| | Leuco-tetrahydroxyanthraquinone | |
|---|---|---|
| | Commercial[1] 1,5/1,8-dihydroxy | Experimental[2] 1,5/1,8-dimethoxy |
| Yield range | 59.5–68.1 grams[3] | 59.4–68.5 grams[4] |
| Average yield | 65.0 grams | 63.7 grams |
| % of theoretical | 65.7% | 64.4% |

[1]Beginning with 87 grams of a mixture of 56% 1,5-dihydroxyanthraquinone and 41% of 1,8-dihydroxyanthraquinone
[2]Beginning with 97 grams of a mixture of 1,5/1,8-dimethoxyanthraquinone
[3]Based on 3 runs
[4]Based on 5 runs It is seen from the above table that the yield range, the average yield and the theoretical yield are equivalent.

We claim:
1. A process for making 1,5-dihydroxy-4,8-diaminoanthraquinone-2,6-disulfonic acid, 1,8-dihydroxy-4,5-diaminoanthraquinone-2,7-disulfonic acid and mixtures thereof, comprising the steps of:
   1. nitrating anthraquinone to give a mixture of dinitroanthraquinones which is about 50-60% 1,5-dinitroanthraquinone, about 30–40% 1,8-dinitroanthraquinone and up to about 20% 1,6- and 1,7-dinitrianthraquinone;
   2. treating the mixture of dinitroanthraquinones with lower alkanolic caustic to convert the nitro groups to lower alkoxy groups and yield a mixture of diloweralkoxy anthraquinones which is predominantly 1,5- and 1,8-diloweralkoxyanthraquinone;
   3. treating the mixture of diloweralkoxy anthraquinones with oleum to yield a mixture of dihydroxyanthraquinone-disulfonic acids which is predominantly 1,5-dihydroxyanthraquinone-2,6-disulfonic acid and 1,8-dihydroxyanthraquinone-2,7-disulfonic acid;
   4. nitrating at least one of the dihydroxyanthraquinonedisulfonic acids to give a dihydroxy-dinitroanthraquinonedisulfonic acid; and
   5. reducing the nitro groups of the dihydroxy-dinitroanthraquinone-disulfonic acid to give a dihydroxy-diaminoanthraquinonedisulfonic acid.

2. The process of claim 1, wherein step (4) is carried out on 1,5-dihydroxyanthraquinone-2,6-disulfonic acid that has been separated from the mixture of dihydroxyanthraquinone-disulfonic acids resulting from step (3).

3. The process of claim 1, wherein step (4) is carried out on the mixture resulting from step (3) to give a mixture of dihydroxy-dinitroanthraquinone-disulfonic acids.

4. The process of claim 3, wherein step (5) is carried out on the mixture of dihydroxy-dinitroanthraquinonedisulfonic acids resulting from step (4).

5. The process of claim 3, wherein step (5) is carried out on 1,5-dihydroxy-4,8-dinitroanthraquinone-2,6-disulfonic acid that has been separated from the mixture of dihydroxy-dinitroanthraquinone-disulfonic acids.

6. A process for making leuco 1,4,5,8-tetrahydroxyanthraquinone which comprises:
   1. nitrating anthraquinone to give a mixture of dinitroanthraquinones which is about 50–60% 1,5-dinitroanthraquinone, about 30–40% 1,8-dinitroanthraquinone and up to about 20% 1,6- and 1,7-dinitroanthraquinone,
   2. treating the mixture of dinitroanthraquinones with lower alkanolic caustic to convert the nitro groups to lower alkoxy groups and yield a mixture of diloweralkoxy anthraquinones which is predominantly 1,5- and 1,8-diloweralkoxyanthraquinone;
   3. treating the mixture of diloweralkoxyanthraquinones with oleum to yield a mixture of dihydroxyanthraquinone-disulfonic acids which is predominantly 1,5-dihydroxyanthraquinone-2,6-disulfonic acid and 1,8-dihydroxyanthraquinone-2,7-disulfonic acid;
   4. nitrating the mixture of the dihydroxyanthraquinonedisulfonic acids to give a mixture of dihydroxy-dinitroanthraquinone-disulfonic acids; and
   5. treating the product mixture of step (4) under reducing conditions to form the lueco-tetrahydroxyanthraquinone.

* * * * *